United States Patent [19]

Copping et al.

[11] 4,139,365

[45] Feb. 13, 1979

[54] METHOD OF REGULATING PLANT GROWTH

[75] Inventors: Leonard G. Copping; John F. Garrod, both of Nottingham, England

[73] Assignee: The Boots Company Limited, Nottingham, England

[21] Appl. No.: 783,084

[22] Filed: Mar. 31, 1977

[30] Foreign Application Priority Data

Apr. 10, 1976 [GB] United Kingdom .............. 14728/76

[51] Int. Cl.$^2$ .......................... A01N 9/22; A01N 5/00
[52] U.S. Cl. ........................................... 71/92; 71/76
[58] Field of Search ...................................... 71/92, 76

[56] References Cited

U.S. PATENT DOCUMENTS

| 3,875,180 | 4/1975 | Munz et al. ............................... 71/92 |
| 3,937,626 | 2/1976 | Barlocher et al. ..................... 71/76 X |

FOREIGN PATENT DOCUMENTS 1469772  4/1977  United Kingdom.

Primary Examiner—Catherine L Mills
Attorney, Agent, or Firm—Lawrence Rosen; E. Janet Berry

[57] ABSTRACT

Regulation in the growth of plants is achieved by use of a composition comprising a growth-regulating amount of a compound having the formula

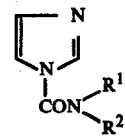

in which $R^1$ is alkyl, alkenyl, optionally substituted phenyl or optionally substituted benzyl and $R^2$ is alkyl, alkenyl, optionally substituted phenyl, optionally substituted benzyl, optionally substituted 2-phenethyl or optionally substituted phenoxyalkyl of the formula $PhO(CH_2)_n$ where $n$ is 2 or 3. The invention is of particular value where the plant is sugar cane or rice.

14 Claims, No Drawings

METHOD OF REGULATING PLANT GROWTH

This invention relates to the regulation of the growth of plants.

A plant growth regulating composition comprises a carrier and a growth-regulating amount of a compound having the formula

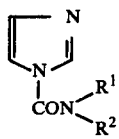

I in which $R^1$ is alkyl, alkenyl, optionally substituted phenyl or optionally substituted benzyl and $R^2$ is alkyl, alkenyl, optionally substituted phenyl, optionally substituted benzyl, optionally substituted 2-phenethyl or optionally substituted phenoxyalky of the formula $PhO(CH_2)_n$ where $n$ is 2 or 3.

A method of regulating plant growth according to the invention comprises applying to the plant a growth regulating amount of such a compound.

These compounds show growth regulating activity on a variety of plants notably sugar cane, rice, tomatoes, sunflowers, sorghum, maize and pot plants for example chrysanthemums and carnations. In one method they are of special use in the improvement of sugar cane. In another method they are of special use in the improvement of rice crops.

The active compound can be applied directly to the plant or to the locus of the plant, in any convenient way that allows uptake by the plant, for instance, by spraying, application of granules to the soil or, when appropriate, by irrigation methods. Treatment takes place at a stage when growth regulation, generally a retardation effect, results in a corresponding increase in crop yield or a convenient reduction in plant size. A reduction in plant size is often an advantage with crops such as rice, sunflowers, sorghum and maize. Under such conditions plant height is reduced which results in a sturdier crop less susceptible to lodging. The size of pot plants and tomatoes can also conveniently be controlled by use of the compounds of formula I. It is often best to apply the active compound to a crop during the early vegetative stage of growth for example at a rate of from ¼ to 20 kilograms per hectare, more preferably at a rate of from 1 to 10 kilograms per hectare.

A preferred method of the invention is one for increasing the sucrose content of sugar cane by applying to the sugar cane a compound of formula I. In this instance the active compound is preferably applied to the crop by addition to the water supply irrigating the land, but other methods can be used such as for example foliar spray treatment or the application of granules to the crop. The active compound has the effect of ripening the crop by increasing the proportion of sucrose in the cane and so it is preferably supplied to the maturing sugar cane shortly before harvest, for example within 10 weeks of harvest and most suitably between 2 and 8 weeks of harvest. The active compound is applied in an amount that results in an increased yield of sucrose and is such as to avoid severe phytotoxic damage to the crop. Amounts depend on the method of application, the stage of growth of the sugar cane and climatic conditions, but in many instances a suitable rate of application of from 1 to 10 kilograms per hectare and preferably from 2 to 8 kilograms per hectare.

A further preferred method of the invention is one for the treatment of rice crops to prevent lodging which comprises applying to the crop a compound of formula I. Most suitably the active compound is supplied to the paddy field in the form of granules or spray, preferably before heading. An application rate of from ½ to 10 kilograms per hectare is preferred and an especially suitable rate is from 1 to 8 kilograms per hectare.

In formula I above, $R^1$ and $R^2$ can be straight or branched chain alkyl groups. An alkyl group contains up to 10 carbon atoms and typical examples include methyl, ethyl, propyl, isopropyl, butyl, isobutyl, sec.butyl, tert.butyl, pentyl, hexyl, octyl, nonyl and decyl. An especially suitable alkyl group contains 1 to 5 carbon atoms.

When $R^1$ or $R^2$ is alkenyl it can be straight or branched chain and preferably contains 3 to 5 carbon atoms. Examples include allyl, 2-methylallyl and 1-propenyl, the most suitable group being allyl.

The groups $R^1$ and $R^2$ can be optionally substituted phenyl or benzyl and also in the case of $R^2$, optionally substituted 2-phenethyl, or phenoxylalkyl of the formula $PhO(CH_2)_n$ where $n$ is 2 or 3. When the group is substituted it includes a phenyl nucleus with one or more, for example 1 to 4, substituents which are the same or different and which include halo (fluorine, chlorine, bromine and iodine), alkoxy, alkyl, trihalomethyl and cyano. Preferably there are 1 to 3 substituents which are the same or different and are halo, alkoxy containing 1 or 2 carbon atoms and alkyl containing 1 to 4 carbon atoms preferably methyl. Amongst these substituents methyl and halo groups are preferred. In particular halo, especially chloro, is the most preferred substituent, one or more of the substituents often being in the 2 or 4 position on the phenyl nucleus.

A group of compounds for use in the invention is one in which $R^1$ is alkyl containing 1 to 5 carbon atoms, alkenyl containing 3 to 5 carbon atoms, optionally substituted phenyl or optionally substituted benzyl, in which the phenyl nucleus is optionally substituted with 1 to 4 substituents which are the same or different and are selected from the group consisting of halo, alkoxy, alkyl trihalomethyl and cyano, and $R^2$ is alkyl containing 1 to 5 carbon atoms, alkenyl containing 3 to 5 carbon atoms, optionally substituted phenyl, optionally substituted benzyl, optionally substituted 2-phenethyl or optionally substituted phenoxyalkyl of the formula $PhO(CH_2)_n$ where $n$ is 2 or 3, in which the phenyl nucleus is optionally substituted with 1 to 4 substituents which are the same or different and are selected from the group consisting of halo, alkoxy, alkyl, trihalomethyl and cyano. The substituents on the phenyl nucleus are preferably chose from halo, alkoxy containing 1 or 2 carbon atoms and alkyl containing 1 to 4 carbon atoms especially methyl. The most preferred substituents are methyl and halo in particular chloro.

A further group of compounds for use in the invention is one in which $R^1$ is alkyl containing 1 to 5 carbon atoms, alkenyl containing 3 to 5 carbon atoms, optionally substituted phenyl or optionally substituted benzyl, in which the phenyl nucleus is optionally substituted with 1 to 4 substituents which are the same or different and are selected from the group consisting of halo, alkoxy, alkyl, trihalomethyl and cyano, and $R^2$ is optionally substituted phenyl, optionally substituted benzyl, optionally substituted 2-phenethyl or optionally substituted 2-phenoxyethyl, in which the phenyl nucleus is optionally substituted with 1 to 4 substituents which are the same or different and are selected from the group consisting of halo, alkoxy, alkyl, trihalomethyl and cyano. The substituents on the phenyl ring are preferably chsoen from halo, alkoxy, containing 1 to 2 carbon atoms and alkyl containing 1 to 4 carbon atoms especially methyl. The most preferred substituents are methyl and halo in particular chloro.

A still further group of useful compounds is one in which $R^1$ is alkyl containing 1 to 5 carbon atoms and $R^2$ is optionally substituted phenyl, optionally substituted benzyl or optionally substituted phenoxyalkyl of the formula $PhO(CH_2)_n$ where $n$ is 2 or 3 in which the phenyl nucleus is optionally substituted with 1 to 4 substituents which are the same or different and are selected from the group consisting of halo, alkoxy, alkyl, trihalomethyl and cyano. The substituents on the phenyl ring are preferably chosen from halo, alkoxy containing 1 to 2 carbon atoms and alkyl containing 1 to 4 carbon atoms especially methyl. The most preferred substituents are methyl and halo in particular chloro.

An especially preferred group of compounds for use in the invention is one in which $R^1$ is alkyl containing 1 to 5 carbon atoms and $R^2$ is optionally substituted benzyl or optionally substituted 2-phenoxyethyl, in which the phenyl nucleus is optionally substituted with 1 to 3 halo or methyl substituents. Particular examples are 1-(N-2-phenoxyethyl-N-propylcarbamoyl) imidazole and 1-(N-2,4-dichlorobenzyl-N-isopropylcarbamoyl) imidazole.

The active compound can be employed as a wide variety of formulations, for example, a solution, a dispersion, an aqueous emulsion, a dispersible powder, an emulsifiable concentrate or granules. Moreover it can be in a form for direct application or as a concentrate which requires dilution with a suitable quantity of water or other diluent before application, for example a concentrate for addition to irrigation water.

As a dispersion, the composition comprises an active compound dispersed in a liquid medium, preferably water. It is often convenient to supply the consumer with a primary composition which can be diluted with water to form a dispersion having the desired concentration. The primary composition can be provided in any one of the following forms. It can be a dispersible solution which comprises the active compound dissolved in a water-miscible solvent with the addition of a dispersing agent. Alternatively it can be a dispersible powder which comprises an active compound and a dispersing agent. A further alternative comprises the active compound in the form of a finely ground powder in association with a dispersing agent and intimatley mixed with water to give a paste or cream which can if desired be added to an emulsion of oil in water to give a dispersion of active ingredient in an aquoeus oil emulsion.

An emulsion comprises an active compound dissolved in a water-immiscible solvent which is formed into an emulsion with water in the presence of an emulsifying agent. An emulsion of the desired concentration can be formed from a primary composition of the following types. A concentrated stock emulsion can be supplied comprising the active compound in combination with an emulsifying agent, water and a water-immiscible solvent. Alternatively an emulsifiable concentrate can be supplied to the user comprising a solution of the active compound in a water-immiscible solvent containing an emulsifying agent.

A granular solid comprises an active compound associated with a solid pulverulent diluent, for example kaolin, and the mixture is granulated by known methods. Alternatively it comprises the active ingredient absorbed, adsorbed or coated on a pre-formed granular diluent, for example, fuller's earth, attapulgite or limestone grit.

More than one active compound can, of course, be included in the composition. In addition the composition can comprise one or more additional plant growth regulator or other active ingredients, with herbicidal, fungicidal, insecticidal or acaricidal properties.

The active ingredients used in the invention are generically disclosed in the literature such as for example British Pat. No. 1,469,772. They can be prepared by a process that comprises reacting imidazole with a carbamoyl halide of the formula $Z-CONR^1R^2$ (II) in which $R^1$ and $R^2$ are as defined in formula I and Z is halogen, for example, chlorine or bromine and preferably chlorine. The reaction is suitably effected in the presence of an inert organic liquid as the reaction medium, which is preferably a solvent for the reactants. Preferably the reaction is carried out in the presence of a suitable acid binding agent, for example a tertiary amine such as triethylamine or pyridine or an excess of imidazole reactant, in order to absorb the hydrogen halide produced in the reaction. Alternatively the reaction can be carried out by first forming an alkali metal derivative of imidazole, for example an N-sodio-derivative, and subsequently reacting it with carbamoyl halide. The reaction can be performed at a temperature of for example from 0° C. to 200° C., and preferably within the range of 50° to 150° C.

The carbamoyl halide of the formula II can be prepared by reacting a secondary amine of the formula $HNR^1R^2$ with a carbonyl halide of the formula $COZ_2$. The secondary amine $HNR^1R^2$ can, in its turn, be prepared in accordance with any of the methods known in the art. For example it can be made by reacting a primary amine of the formula $R^1NH_2$ or $R^2NH_2$ with the respective alkyl halide of the formula $R^2Q$ or $R^1Q$, in which Q is halogen, preferably bromine.

The method of the invention is illustraded by the following Examples.

EXAMPLE 1

(a) Sugar cane sets were grown under controlled conditions in pots containing compost. The plants were allowed to develop for six weeks and the soil surrounding the canes was then treated with aqueous dispersions of the compounds 1-(N-2,4-dichlorobenzyl-N-isopropylcarbamoyl)imidazole (compound A) and 1-(N-2-phenoxyethyl-N-propylcarbamoyl)imidazole (compound B) at rates equivalent to 4 and 8 kilograms per hectare. After a further six weeks the plants were harvested and measurements of the length in centimeters of the first six internodes recorded. A significant retardation of growth was observed in plants treated with compounds A and B.

|  | compound A | | compound B | | control |
|---|---|---|---|---|---|
|  | 4 kg | 8 kg | 4 kg | 8 kg |  |
| length (cm) | 14.90 | 12.40 | 12.43 | 11.77 | 18.13 |

(b) Samples of compounds A and B were also evaluated on field growth sugar cane to determine their ripening properties. The compounds were applied at a rate of 4 lb per acre through a simulated irrigation system. Harvests were made at intervals after application and sucrose concentration determined (percent cane as determined by polarimetry).

| Weeks after application | sucrose concentration | | |
|---|---|---|---|
| | compound A | compound B | control |
| 0 | — | — | 5.6 |
| 4 | 10.58 | 10.27 | 7.12 |
| 7 | 11.29 | 11.22 | 10.58 |

The above results clearly indicate that a significant improvement in the concentration of sucrose occurs when compounds A and B were applied to the sugar cane.

EXAMPLE 2

In a field trial, sugar cane was treated at a rate of 4 lb per acre by sub-surface irrigation with the compound 1-(N-2-phenoxyethyl-N-propylcarbamoyl) imidazole. Samples of cane were taken at regular intervals and juice purity and sucrose concentration determined.

The former quantity is a measure of the amount of sucrose present, being the percentage sucrose in the total soluble solids in the juice expressed from the sample of sugar cane. It is calculated by determining the total soluble solid content by means of refractometry and with a knowledge of sucrose concentration determined by polarimetry.

Sucrose concentration is the percentage of sucrose per unit weight of fresh cane.

| Time after application (weeks) | Treatment | Juice purity | Sucrose concentration |
|---|---|---|---|
| 0 | active compound | 73.90 | 8.04 |
| | control | 72.33 | 7.49 |
| 2 | active compound | 71.63 | 6.90 |
| | control | 69.19 | 6.40 |
| 3 | active compound | 77.54 | 8.69 |
| | control | 74.51 | 7.83 |
| 4 | active compound | 73.32 | 7.65 |
| | control | 66.54 | 6.17 |

The above observations demonstrate that the active compound increases the sucrose content of sugar cane. It improves the crop in two important respects by increasing the proportion of sucrose in the extracted juice and by increasing the quantity of sucrose produced. An improvement in juice purity also aids processing and extraction of sucrose from the sugar cane.

EXAMPLE 3

In an experiment to demonstrate the crop regulating activity of compounds on rice, rice plants were grown in pots containing low organic content compost. The temperature conditions were controlled with a daytime temperature of 28° C. and a temperature of 18° C. at night. Approximately 15 days before heading out, the plants were treated with the two compounds 1-(N-2,4-dichlorobenzyl-N-isopropylcarbamoyl)imidazole (compound A) and 1-(N-2-phenoxyethyl-N-propylcarbamoyl)imidazole (compound B) as a soil drench at rates of 4, 2, 1 and ½ lb/acre. The height of the plants was recorded two and four weeks after treatment and the following results obtained:

| | control | Plant height (centimeters) | | | | | | | |
|---|---|---|---|---|---|---|---|---|---|
| | | compound A | | | | compound B | | | |
| | | 4 lb | 2 lb | 1 lb | ½ lb | 4 lb | 2 lb | 1 lb | ½ lb |
| 2 weeks | 35.2 | 25.7 | 31.5 | 31.2 | 33.5 | 21.5 | 23.0 | 26.0 | 28.2 |
| 4 weeks | 45.2 | 26.7 | 35.7 | 37.0 | 40.5 | 37.2 | 40.0 | 37.0 | 39.7 |

No adverse effect on the yield of the rice plants was observed.

EXAMPLE 4

Young sunflower seedlings were supported above aqueous solutions active compounds at concentration of 100 mg/liter in small plastic pots. The seedlings were covered with a layer of vermiculite and incubated in a controlled environment for 10 days at 25° C. At the end of the growing period an assessment of the reduction in plant height was made.

All of the following compounds reduced the height of the seedlings at least 50 percent by comparison with the control.

1-[N-3-(4-bromophenoxy)propyl-N-isopropylcarbamoyl]imidazole

1-[N-butyl-N-2-(2,4,6-trichlorophenoxy)ethylcarbamoyl]imidazole

1-[N-pentyl-N-2-(2,4,6-trichlorophenoxy)ethylcarbamoyl]imidazole

1-[N-2-(4-iodophenoxy)ethyl-N-propylcarbamoyl]imidazole

1-[N-allyl-N-2-(2,4-dichloro-6-methylphenoxy)ethylcarbamoyl]imidazole

1-[N-2-(2,6-dibromo-4-fluorophenoxy)ethyl-N-propylcarbamoyl]imidazole

EXAMPLE 5

Sorghum plants were grown in 3½ inch diameter pots in compost containing a low proportion of organic matter. The environmental conditions were controlled at a temperature of 27° C. during the day and 18° C. at night. Aqueous drenches were applied to the pots at rates equivalent to 4, 2, 1 and ½ lb/acre of active compound, with the following results.

The height of the plants was measured in comparison with that of controls at two and four weeks after treatment.

| | control | Plant height (centimeters) | | | | | | | |
|---|---|---|---|---|---|---|---|---|---|
| | | compound A | | | | compound B | | | |
| | | 4 lb | 2 lb | 1 lb | ½ lb | 4 lb | 2 lb | 1 lb | ½ lb |
| 2 weeks | 52.2 | 27.7 | 46.2 | 44.0 | 48.7 | 35.0 | 43.2 | 42.0 | 45.0 |

| | control | compound A | | | | compound B | | | |
|---|---|---|---|---|---|---|---|---|---|
| | | Plant height (centimeters) | | | | | | | |
| 4 weeks | 62.7 | 47.0 | 55.0 | 57.2 | 63.7 | 56.0 | 60.7 | 56.0 | 56.7 |

Compound A was 1-(N-2,4-dichlorobenzyl-N-isopropylcarbamoyl)imidazole
Compound B was 1-(N-2-phenoxyethyl-N-propylcarbamoyl)imidazole

EXAMPLE 6

Tests were carried out to demonstrate the growth regulating properties of compounds on tomato plants.

Tomato plants were grown in a low organic matter compost in pots in the glasshouse. At the 4 leaf stage plants were selected for uniformity of growth and active compounds applied as an aqueous drench to the soil at 15 mg/pot. Four replicates were carried out for each treatment and after periods of 2 and 4 weeks from the time of application the height of plants was assessed in comparison with controls.

The following compounds all reduced the height of plants by more than 25 percent ($R^1$ and $R^2$ refer to formula I above).

| $R^1$ | $R^2$ |
|---|---|
| phenyl | 4-fluorophenyl |
| methyl | 4-bromophenyl |
| propyl | phenyl |
| methyl | 4-chlorophenyl |
| propyl | 2-chlorophenyl |
| butyl | butyl |
| isopropyl | isopropyl |
| propyl | propyl |
| allyl | allyl |
| methyl | hexyl |
| hexyl | hexyl |
| butyl | allyl |
| propyl | 2-propynyl |
| benzyl | 2-(2,4-dichlorophenoxy)ethyl |
| benzyl | 2-phenoxyethyl |
| methyl | 4-methoxy |
| methyl | 4-chlorobenzyl |
| ethyl | 4-chlorobenzyl |
| ethyl | benzyl |
| isopropyl | benzyl |
| allyl | 4-chlorobenzyl |
| isopropyl | 4-chlorobenzyl |
| allyl | 2-methylphenyl |
| methyl | 2-phenethyl |
| benzyl | 2-phenethyl |
| phenyl | 2,4-dichlorobenzyl |
| phenyl | benzyl |
| benzyl | 4-methylbenzyl |

What is claimed is:

1. A method of regulating plant growth which comprises applying to a plant selected from the group consisting of sugar cane, rice, tomatoes, sunflowers, sorghum, maize and pot plants a growth-regulating amount of a compound having the formula

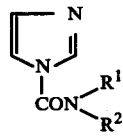

in which $R^1$ is selected from the group consisting of alkyl containing 1 to 10 carbon atoms, alkenyl containing 3 to 5 carbon atoms, optionally substituted phenyl and benzyl, wherein the substituted phenyl nucleus has 1 to 4 substituents selected from the group consisting of halo, alkoxy containing 1 or 2 carbon atoms, alkyl containing 1 to 4 carbon atoms, trihalomethyl and cyano, and $R^2$ is selected from the group consisting of alkyl containing 1 to 10 carbon atoms, alkenyl containing 3 to 5 carbon atoms, optionally substituted phenyl, benzyl, 2-phenethyl and phenoxyalkyl of the formula $PhO(CH_2)_n$ where $n$ is 2 or 3, wherein the substituted phenyl nucleus has 1 to 4 substituents selected from the group consisting of halo, alkoxy containing 1 to 2 carbon atoms, alkyl containing 1 to 4 carbon atoms, trihalomethyl and cyano, whereby the crop yield of the plant is increased or the plant size is reduced.

2. A method according to claim 1 wherein the plant is selected from the group consisting of sugar cane, rice, tomatoes, sunflowers, and sorghum.

3. A method according to claim 1 in which the plant is sugar cane.

4. A method according to claim 1 in which the plant is rice.

5. A method according to claim 1 in which $R^1$ is alkyl, alkenyl, optionally substituted phenyl or optionally substituted benzyl and $R^2$ is optionally substituted phenyl, optionally substituted benzyl, optionally substituted 2-phenethyl or optionally substituted 2-phenoxyethyl.

6. A method according to claim 5 in which $R^1$ is alkyl containing 1 to 5 carbon atoms and $R^2$ is optionally substituted benzyl or optionally substituted 2-phenoxyethyl, in which the phenyl nucleus is optionally substituted with 1 to 3 substituents which are the same or different and are halo or methyl.

7. A method for increasing the sucrose content of sugar cane by applying to the sugar cane a compound as defined in claim 5.

8. A method according to claim 7 in which $R^1$ is alkyl containing 1 to 5 carbon atoms and $R^2$ is optionally substituted benzyl or optionally substituted 2-phenoxyethyl, in which the phenyl nucleus is optionally substituted with 1 to 3 substituents which are the same or different and are halo or methyl.

9. A method according to claim 8 which comprises applying 1-(N-2-phenoxyethyl-N-propylcarbamoyl)imidazole or 1-(N-2,4-dichlorobenzyl-N-isopropylcarbamoyl)imidazole.

10. A method according to claim 7 which comprises applying the compound betweens 2 and 8 weeks of harvest and at a rate of 2 to 8 kilograms per hectare.

11. A method for the treatment of rice crops to prevent lodging which comprises applying to the crop a compound as defined in claim 6.

12. A method according to claim 11 in which $R^1$ is alkyl containing 1 to 5 carbon atoms and $R^2$ is optionally substituted benzyl or optionally substituted 2-phenoxyethyl in which the phenyl nucleus is optionally substituted with 1 to 3 substituents which are the same or different and are halo or methyl.

13. A method according to claim 11 which comprises applying 1-(N-2-phenoxyethyl-N-propylcarbamoyl)imidazole or 1-(N-2,4-dichlorobenzyl-N-isopropylcarbamoyl)imidazole.

14. A method according to claim 11 which comprises applying the compound at a rate of 1 to 8 kilograms per hectare.

* * * * *